(12) United States Patent
Casu et al.

(10) Patent No.: US 8,222,231 B2
(45) Date of Patent: *Jul. 17, 2012

(54) DERIVATIVES OF PARTIALLY DESULPHATED GLYCOSAMINOGLYCANS ENDOWED WITH ANTIANGIOGENIC ACTIVITY AND DEVOID OF ANTICOAGULATING EFFECT

(75) Inventors: Benito Casu, Milan (IT); Giangiacomo Torri, Milan (IT); Anna Maria Naggi, Milan (IT); Giuseppe Giannini, Rome (IT); Claudio Pisano, Rome (IT); Sergio Penco, Milan (IT)

(73) Assignee: Sigma-Tau Industrie Farmaceutiche Riunite SpA, Rome (IT)

( * ) Notice: Subject to any disclaimer, the term of this patent is extended or adjusted under 35 U.S.C. 154(b) by 0 days.

This patent is subject to a terminal disclaimer.

(21) Appl. No.: 12/851,166

(22) Filed: Aug. 5, 2010

(65) Prior Publication Data
US 2010/0298263 A1 Nov. 25, 2010

Related U.S. Application Data

(60) Division of application No. 11/028,512, filed on Jan. 4, 2005, now Pat. No. 7,790,700, which is a continuation-in-part of application No. 10/967,255, filed on Oct. 19, 2004, now abandoned, which is a continuation of application No. 10/182,185, filed as application No. PCT/IT01/00034 on Jan. 24, 2001, now abandoned.

(30) Foreign Application Priority Data

Jan. 25, 2000 (IT) .................................. RM00A0041

(51) Int. Cl.
A61K 31/727 (2006.01)
A61K 31/715 (2006.01)
A61P 39/00 (2006.01)
(52) U.S. Cl. .............................. 514/56; 514/54; 536/18.7
(58) Field of Classification Search .................... 514/54, 514/56; 536/18.7
See application file for complete search history.

(56) References Cited

U.S. PATENT DOCUMENTS

| 4,500,519 | A | | 2/1985 | Lormeau et al. | |
|---|---|---|---|---|---|
| 5,280,016 | A | * | 1/1994 | Conrad et al. | 514/56 |
| 5,583,121 | A | * | 12/1996 | Chaudry et al. | 514/56 |
| 5,668,118 | A | | 9/1997 | Kennedy | |
| 5,808,021 | A | | 9/1998 | Holme et al. | |
| 5,854,221 | A | * | 12/1998 | Cao et al. | 514/13.3 |
| 5,912,237 | A | | 6/1999 | Kennedy | |
| 7,781,416 | B2 | * | 8/2010 | Casu et al. | 514/54 |
| 7,790,700 | B2 | * | 9/2010 | Casu et al. | 514/56 |
| 2002/0010152 | A1 | | 1/2002 | De Ambrosi et al. | |

FOREIGN PATENT DOCUMENTS

| EP | 0 254 067 | 1/1988 |
|---|---|---|
| JP | 6-157344 A | 6/1994 |
| JP | 512822 | 12/1997 |
| JP | 10218902 | 8/1998 |
| JP | 11-511172 A1 | 9/1999 |
| WO | 88/01280 | 2/1988 |
| WO | 92/01003 | 1/1992 |
| WO | 94/14851 | 7/1994 |
| WO | 95/02613 | 1/1995 |
| WO | 96/06867 | 3/1996 |
| WO | 9606867 A1 | 3/1996 |
| WO | 9726258 A1 | 7/1997 |
| WO | 99/27976 | 6/1999 |
| WO | 9927976 A1 | 6/1999 |
| WO | 01/55221 | 8/2001 |

OTHER PUBLICATIONS

Ribatti, D. et al., "TheChick Embryo Chorioallantoic Membrane as a Model for in vivo Research on Anti-Angiogenesis" Current Pharmaceutical Biotechnology, 2000, pp. 73-82.
Strum, J. et al., "Angiogenic Responses Elicited From Chorioallantoic Membrane Vessels by Neoplastic, Preneoplastic and Normal Mammary Tissues from GR Mice" Am J. Pathology 1983, 111:282-287, pp. 282-287.

(Continued)

Primary Examiner — Shaojia Anna Jiang
Assistant Examiner — Ganapathy Krishnan
(74) Attorney, Agent, or Firm — Lucas & Mercanti, LLP

(57) ABSTRACT

Partially desulfated glycosaminoglycan derivatives are described, particularly heparin, and more particularly formula (I) compounds

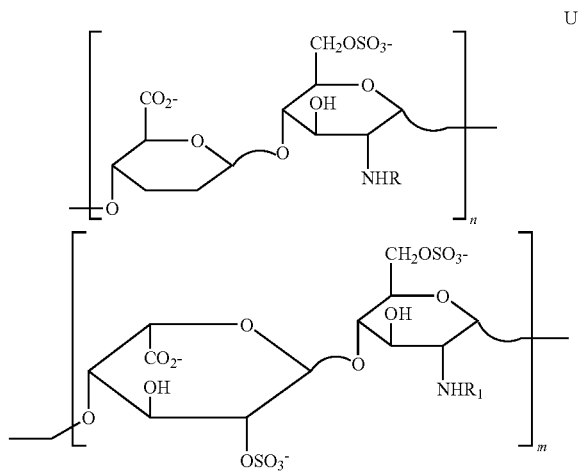

where the U, R and $R_1$ groups have the meanings indicated in the description. These glycosaminoglycan derivatives exhibit antiangiogenic activity and are devoid of anticoagulant activity.

11 Claims, 1 Drawing Sheet

OTHER PUBLICATIONS

Lugassy, C. et al., "Pericyte-Like Location of GFP-Tagged Melanoma" Am J. Pathology, vol. 164, No. 4, Apr. 2004, p. 1191-1198.

Marks, M. et al., "Effects of Putative Hydroxylated Thalidomide Metaboites on Blood Vessel Density in the Chorioallantoic Membrane (CAM) Assay and on Tumor and Endothelial Cell Proliferation" Biol. Pharm. Bill. 25(5) 597-604 (2002), pp. 597-604.

Miller, W. et al., "A novel technique for quantifying changes in vascular density, endothelial cell proliferation and protein expression in response to modulators of angiogenesis using chick chorioallantoic membrane (CAM) assay" Journal of Translational Medicine 2004, 2:4, Jan. 2004.

Swiercz, R. et al., "Angiostatic activity of synthetic inhibitors of urokinase type plasminogen activator" Oncology Reports 6: 523-526, 1999.

Fransson, L. et al., "Periodate and alkaline degradation of heparin-related glycans" Carbohyd. Res. (1980) vol. 80, pp. 131-145.

Fransson, L. et al., "Relationship between anticoagulant activity of heparin and susceptibility to periodate oxidation" FEBS Lett. (1979) vol. 97, No. 1, pp. 119-123.

Casu, B. et al., "Retention of Antilipemic activity by periodate-oxidized non-anticoagulant heparins" Arzneim.-Forsch./ Drug Res., vol. 36, No. 1, pp. 637-642.

Jaseja, M., et al. "Novel regio- and steroselective modifications of heparin in alkaline solution. Nuclear magnetic resonance spectroscopic evidence", Canadian Journal of Chemistry, Jan. 1989, vol. 67. pp. 1449-1456.

* cited by examiner

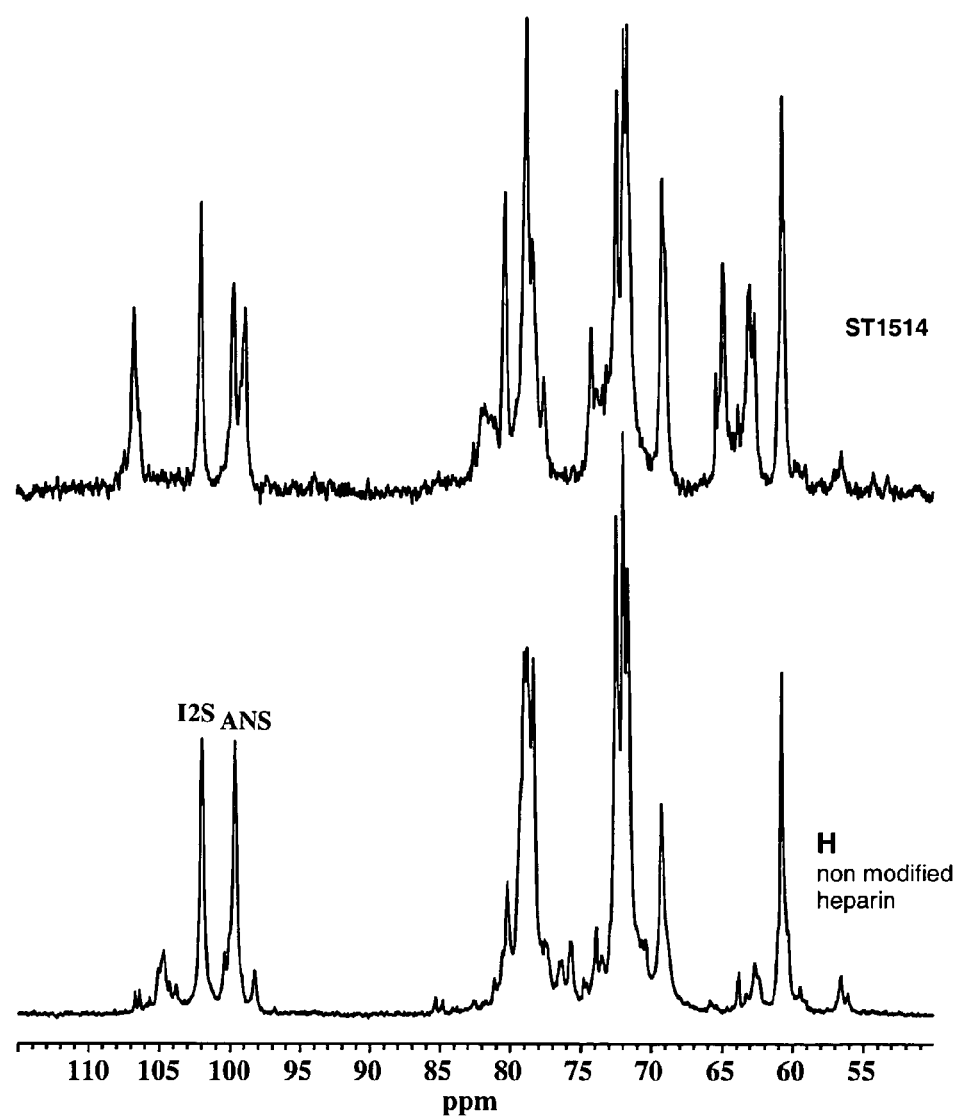

DERIVATIVES OF PARTIALLY DESULPHATED GLYCOSAMINOGLYCANS ENDOWED WITH ANTIANGIOGENIC ACTIVITY AND DEVOID OF ANTICOAGULATING EFFECT

CROSS REFERENCE TO RELATED APPLICATIONS

This application is a divisional of U.S. application Ser. No. 11/028,512 filed Jan. 4, 2005, which is a continuation-in-part of U.S. application Ser. No. 10/967,255 filed Oct. 19, 2004, which is a continuation of U.S. application Ser. No. 10/182,185 filed Jul. 25, 2002, now abandoned, which is a 371 of PCT/IT01/00034 filed Jan. 24, 2001 which claims benefit of priority of Italian application RM2000A000041 filed Jan. 25, 2000, the entire contents of the aforementioned applications are hereby incorporated by reference into this application.

The invention described herein relates to partly desulfated 10 glycosaminoglycan derivatives, particularly heparins, to processes for their preparation, to their use as active ingredients for the preparation of medicaments with an antiangiogenic activity, particularly for the treatment of tumors, such as, for example, the metastatic forms, and to pharmaceutical compositions containing them.

BACKGROUND OF THE INVENTION

The first molecule possessing antiangiogenic activity was discovered in cartilage by Henry Brem and Judah Folkman in 1975. Since that year more than 300 new molecules capable of inhibiting angiogenesis have been discovered.

In the early eighties, with the discovery of interferon ($\alpha/\beta$) as an inhibitor of tumor angiogenesis, clinical experimentation was initiated based on this therapeutic approach.

The media caused quite a stir, when on 3 Mar. 1998 the NewYork Times published the news that two molecules, angiostatin and endostatin, discovered in J. Folkman's laboratories at the Harvard Medical School and Children's Hospital in Boston, were yielding very encouraging results in the struggle against cancer. The high degree of efficacy of these two molecules in inhibiting angiogenesis substantially boosted the search for new compounds. At present, there are about thirty molecules endowed with anticancer activity which act via an antiangiogenic mechanism, which have entered into the clinical trials stage [Phases I-III] and almost the same number of companies and institutions are involved.

In the United States alone it is estimated that there are approximately 9 million patients who could benefit from antiangiogenic therapy. At the present time, at least 4,000 patients have been enrolled into clinical trials using this therapy without any particular unwanted effects being registered.

Within the framework of the general concept of angiogenesis we should distinguish between vasculogenesis, that is to say the formation of blood vessels during embryonic development and angiogenesis in the strict sense of the term, meaning the formation of new blood vessels (capillaries) during the postnatal life starting from pre-existing vessels. The importance of angiogenesis for the growth of solid tumors is amply documented. Over the past three decades it has been reported that tumor growth, as well as the formation of metastases, are strictly dependent on the development of new vessels capable of vascularising the tumor mass.

The inhibition of angiogenesis underlies the formation of necrotic masses within the tumor or the induction of apoptosis in tumor cells.

There are clear-cut differences between neovascularisation in normal tissue and that in tumor tissue. In the former, the vascular endothelium represents a quiescent tissue with a very low mitotic index of its constituent cells (renewal time measured in hundreds of days), and the vascular network is regular, relatively uniform, and suitable for adequately oxygenating all the tissues, without any arteriovenous connection. In tumor tissue, on the other hand, stimulation of the proliferation of endothelial cells gives rise to a high mitotic index in the latter (mean renewal time 5 days), the neovascularisation is distinctly irregular with areas of occlusion, sometimes with closed endings, with arteriovenous contacts at some points, and, lastly, the basal membrane presents gaps, which at some points leads to tissue hypoxia. These differences offer the opportunity of identifying drugs which selectively block tumor neovascularisation.

In a tumor, the neovascularisation does not always coincide with a precise stage in the tumor development; there are, in fact, cases in which angiogenysis begins even before the development of the tumor (for example, carcinoma of the uterine cervix), others in which the two phases are coincident (for example, carcinoma of the bladder and breast), and others in which angiogenesis begins after the neoplasm (for example, melanoma and ovarian carcinoma; see, for example, "Manual of Medical Oncology", IV ed. (1991) G. Bonadonna et al.

Antiangiogenic therapy presents numerous advantages compared to traditional standard chemotherapy (Cancer Research 1998, 58, 31408-16):

a) specificity: its target is a process, i.e. tumor neovascularisation;

b) bioavailability: its target is the endothelial cells, which can be easily reached without the problems of traditional chemotherapy which acts directly on the tumor cells;

c) chemoresistance: this is perhaps the most important advantage of this therapy; in fact, since endothelial cells, unlike tumor cells, are genetically stable, drug resistance phenomena are unlikely to occur;

d) metastatic spread: blockade of the neovascularisation limits the propagation of the tumor cells to other parts of the body via the bloodstream;

e) apoptosis: blockade of the vascular network in the tumor reduces the supply of oxygen and nutrients to the tumor cells; apoptosis is favored in these conditions;

f) reduced systemic tOxicity: toxic effects, such as myelosuppression, gastrointestinal effects and temporary hair loss, which are almost invariably present with traditional chemotherapy, are not observed with antiangiogenic therapy.

A number of molecular elements are known to be involved in tumor angiogenesis (Oncology 1997, 54, 177-84). Pro- and anti-angiogenic endogenous factors are known to be involved in the biological regulatory mechanism in the formation of new vessels.

Among the angiogenic stimulators we should mention: fibroblast growth factors (FGF), vascular endothelial growth factor (VEGF), angiogenin, transforming growth factor-a, tumornecrosis factor (TNF-$\alpha$), platelet-derived endothelial cell growth factor, transforming growth factor-$\beta$, an in-vitro inhibitor, but an in-vivo stimulator, placental growth factor, interleukin-8, hepatocyte growth factor, platelet-derived growth factor, granulocyte colony-stimulating factors, proliferin, the prostaglandins ($PGE_1$, $PGE_2$), GM1-GT1b, substance P, the bradykinins, and nitric oxide.

In contrast, the angiogenesis inhibitors include: the soluble receptor of bFGF, the interferons ($\alpha$, $\beta$, $\gamma$), angiostatin, thrombospondin1, prolactin (16 kDa terminal amino fragment), platelet factor 4 (PF4), the tissue metalloproteinase (TIMP)

inhibitors, placental proliferinrelated peptide, glioma-derived angiogenesis inhibition factor, the angiostatic steroids, cartilage-derived inhibitor (CDI), the heparinases, 5 interleukin-12, plasminogen activator inhibitor, the retinoids, endostatin, angiopoietin-2, genistein, nitric oxide and GM3.

The integrins are a vast family of transmembrane proteins that mediate cell-to-cell and cell-to-extracellular matrix interactions. All integrins are capable of recognising a common peptide sequence Arg-Gly-Asp ("universal cell recognition site"), though every integrin preferentially recognizes a different conformation of this tripeptide. The inhibition of specific subtypes of integrins can also be of great interest from the pharmacological standpoint for the development of angiogenesis inhibitors.

The control of protein kinase-C (PK-C) may also allow regulation of angiogenesis. There are, in fact, classic PK-C inhibitors capable of completely or partially blocking angiogenesis.

Despite the enormous investments and the involvement of large numbers of institutional and private research centers, the cancer problem world-wide is still far from being definitively solved. Though the prognosis of cancer victims has improved, with survival rates rising over the past 30 years on average from 30 to 50%, and the genetic, cellular and biochemical mechanisms involved in the development of a tumor are now well known, the possibility of defeating or at least limiting this type of pathology is still a problem of keenly felt concern and many aspects are still unsolved, such as the likelihood of recurrence, complete remission and metastatic spread of the primary tumor.

Since the late seventies, when Folkman's observations began to be confirmed by the international scientific community, hundreds of molecules endowed with antiangiogenic activity have been isolated from natural sources (plants, fungi, biological fluids) and synthesized in the laboratory.

A number of drugs are already in Phase III, such as Marimastat (British Biotech.), l'AG3340 (Prinomast-Agouron), and Neovastat (Aeterna), all of which act mainly at the pulmonary level (SNCL) with a mechanism involving interference with the metalloproteinases. Also in Phase III are RhuMad VEGF (this is an anti-VEGF antibody by Genetech) and interferon α (commercial), which are active against solid tumors thanks to their interference with pro-angiogenic growth factors, or TNP-470 (TAP Pharm.) which acts directly on the endothelial cells. Lastly, drugs such as CAI (NCI) and IM862 (Cytran) are active as antiangiogenic agents but with a non-specific and poorly known mechanism.

These above-mentioned drugs may, in a few years, become part of the oncologist's therapeutic armamentarium, but there are other molecules which have recently been inserted in Phase I/II clinical trials such as Combretastatin (OxiGene), methoxy-oestradiol and endostatin (EntreMed), which on the basis of preclinical studies are very promising. Companies such as Bristol Myers-Squibb (with BMS-275291), Novartis (with CGS27023A) or Parke-Davis (with Suramin) are involved in this therapeutic strategy.

Heparin

Heparin is a heterogeneous mixture of naturally occurring polysaccharides of various lengths and various degrees of sulphation which possesses anticoagulant activity and is secreted by the connective tissue mastcells present in the liver (from which it was first isolated), in the muscles, lungs, thymus and spleen.

In addition to the regular sequence, a sequence corresponding to the active site for antithrombin activity has been identified in heparin.

The antitumorand antimetastatic activity of heparin and its derivatives is due to its ability to inhibit heparanase, to block growth factors and to regulate angiogenesis.

Heparan Sulphates (HS)

Heparan sulphates (HS) are ubiquitous protein ligands. The proteins bind to the HS chains for a variety of actions from simple immobilisation or protection against the proteolytic degradation action to specific modulations of biological activities, such as angiogenesis.

The carbohydrate skeleton, in both heparin and the heparin sulphates (HS), consists in an alternation of D-glucosamine (GlcN) and hexuronic acids (Glc.A or IdO.A).

In heparin, the GlcN residues are mainly N-sulphated, whereas in HS they are both N-sulphated and N-acetylated, with a small amount of unsubstituted N—.

HS is also on average less O-sulphated than heparin.

The use of heparin in the treatment of angiogenesis disorders, such as tumors, particularly metastases, is substantially limited by the anticoagulant activity of heparin.

Chemical modifications have been made to heparin so as to reduce its anticoagulant capacity, at the same time preserving its antitumorproperties.

The opening of a unit of glucuronic acid in the antithrombin site reduces the affinity of heparin for antithrombin: in this way, heparins can be used with reduced anticoagulant effects, but still retaining antiangiogenic properties.

Heparanases

"Heparanases" are enzymes belonging to a family of endoglycosidases that hydrolyse the internal glycoside bonds of the chains of heparan sulphates (HS) and heparin.

These endoglycosidases are involved in the proliferation of tumor cells, in metastases and in the neovascularisation of tumors. This suggests they may also be involved in tumor angiogenesis as a result of the release, from the extracellular matrix, of growth factors bound to heparin, such as aFGF (also called FGF-1), bFGF (also called FGF-2) and VEGF.

These enzymes are biological targets for antiangiogenic activity. In the scientific literature there are a large number of structure/activity correlation studies (see, for example, Lapierre F. et al., *Glycobiology*, vol. 6, (3), 355-366, 1996). Though many aspects have still to be clarified, studies have been reported regarding the inhibition of heparanases by heparin and its derivatives, using specific tests which have led to the emergence of considerations of a structural type which may serve as guides for obtaining new, more selective derivatives.

In the above mentioned work of Lapierre et al., heparin derivatives are described obtained by 2-O desulfation or by "glycol split" (oxidation with periodate and subsequent reduction with sodium borohydride). These derivatives, defined here as "2-O-desulfated heparin" and "RO-heparin", respectively, have partly maintained the antiangiogenic activity of heparin as assessed by means of the CAM test in the presence of corticosteroids, as reported in Table III (ibid. page 360).

Heparins and FGF

FGFs regulate multiple physiological processes such as cell growth and differentiation, but also functions involved in pathological processes such as tumorangiogenesis.

FGFs are growth factors (a family of more than 10 polypeptides, of which the acid (FGF-1) and basic FGFs (FGF-2) are the ones which have been most studied, which require a polysaccharide cofactor, heparin or HS, to bind to the FGF receptor (FGFR) and activate it.

Though the precise mechanism whereby heparin and HS activate FGFs is unknown, it is known, however, that heparin/FGF/FGFR form a "trimolecular" or "ternary" complex.

One mechanism postulated is that heparin and HS induce so-called sandwich dimerisation of FGF, and the latter, thus dimerised, forms a stable complex with FGFR.

Antimetastatic Activity of Heparin Derivatives

The ability of a primary tumor to generate metastatic cells is perhaps the main problem facing anticancer therapy.

Heparin derivatives with a substantial ability to block heparanase seem to be equally capable of inhibiting angiogenesis both in primary tumors and in metastases.

In addition, the inhibition of heparanase reduces the migration ability of tumor cells from the primary tumor to other organs.

The following table gives an example of structure/antimetastatic activity correlation in the case of heparin:

|  | % inhibition |
| --- | --- |
| Heparin | 97 |
| N-succinyl-heparin | 60 |
| N-succinyl-RO-heparin | 58 |
| Low MW heparin | 86 |
| Low MW N-succinyl-heparin | 61 |
| Very low MW heparin | 83 |

MW = molecular weight

The data in this table suggest that very short fragments of heparin are still endowed with good antimetastatic activity, while this activity is reduced when the amine group of the glucosamine is bound to succinic acid.

The structural requisites of heparin-like molecules that favor the angiogenesis-inhibiting action can be grouped in two categories on the basis of the target one intends to block:

a) blockade of heparanase, an enzyme that hydrolyses the glycoside bonds of the heparan sulphates, releasing growth factors.

To this end the heparin-like compounds preferably comprise sequences of at least eight monosaccharide units containing N-acetyl-glucosamine-glucuronic acid (or N-sulphated glucosamine (see, for example, D. Sandback-Pikas et al. J. Biol. Chem., 273, 18777-18780 (1998) and references cited).

b) blockade of angiogenic growth factors (fibroblast type: FGF-1 and FGF-2; vascular endothelium type: VEGF; vascular permeability type: VPF).

To this end the heparin-like compounds preferably have sequences at least five monosaccharide units long, containing 2-suplhated iduronic acid and glucosamine N, 6-sulphated (see, for example, M. Maccarana et al. J. Bill. Chem., 268, 23989-23905 (1993)).

In the literature small peptides (5-13 amino acids) with antiangiogenic activity (U.S. Pat. No. 5,399,667 of the University of Washington) which act by binding to a thrombospondin receptor, or longer peptides (50 amino acids approx.).

Modified platelet factors are known—(EP 0 589 719, Lilly), capable of inhibiting endothelial proliferation, with $IC_{50}$=7 nM.

Oligosaccharide fragments with antiangiogenic activity have also been amply described: it has been found, in fact, that by varying the carbohydrate sequence the interaction selectivity can be increased.

In addition, heparin can be used as a vehicle for substances which are themselves antiangiogenic, such as some steroids, exploiting the affinity of heparin for vascular endothelial cells; see, for example, WO 93/18793 of the University of Texas and Imperial Cancer Research Technology, where heparins are claimed with acid-labile linkers, such as adipic acid hydrazine, bound to cortisol. The antiangiogenic effect of the conjugated molecules is greater than that of the unconjugated molecules, even when administered simultaneously.

In Biochim. Biophys. Acta (1996), 1310, 86-96, heparins bound to steroids (e.g. cortisol) are described with a hydrazone group in C-20 that present greater antiangiogenic activity than the two unconconjugated molecules.

EP 0 246 654 by Daiichi Sc. describes sulphated polysaccharides with antiangiogenic activity with Phase II studies.

EP 0 394 971 by Pharmacia & Upjohn—Harvard Coll. Describes hexa-saccharides-heparin fragments—with low sulphation, capable of inhibiting the growth of endothelial cells and angiogenesis stimulated by (FGF-1).

EP 0 618 234 by Alfa Wasserman describes a method for preparing semisynthetic glycosaminoglycans with a heparin or heparin structure bearing a nucleophilic group.

WO 95/05182 by Glycomed describes various sulphated oligosaccharides with anticoagulant, antiangiogenic and anti-inflammatory activity.

U.S. Pat. No. 5,808,021 by Glycomed describes a method for preparing substantially non-depolymerised 2-O, 3-O desulfated heparin with a desulfation percentage in positions 2- of the iduronic acid (1, 2-O) and in position 3 of the glucosamine unit (A, 3-O) ranging from approximately 99 to approximately 75% of the original percentage. This method envisages desulfation conducted in the presence of a cation of a bivalent metal, exemplified by calcium or copper, followed by lyophilisation of the product obtained. The desulfated heparins have antiangiogenic activity.

The aim of the invention described herein is to find optimal glycosaminoglycan structures for generating antiangiogenic activity based on heparanase inhibition and/or FGF growth factor inhibition mechanisms. An additional aim of the invention described herein is to provide a medicament with antiangiogenic activity which is essentially devoid of the typical side effects of heparin derivatives, such as, for example, anticoagulant activity.

BRIEF DESCRIPTION OF THE DRAWINGS

FIG. 1 is a graph of the NMR spectroscopy of the compound ST1514 and of a non-modified heparin.

SUMMARY OF THE INVENTION

It has now been found that on subjecting a glycosaminoglycan, such as a heparin-like glycosaminoglycan, heparin or modified heparin, containing glucosamine residues with different degrees of N-desulfation and optional subsequent total or partial N-acetylation, to controlled 2-O-desulfation treatment of the iduronic units up to a degree of desulfation not greater than 60% of the total uronic units, the angiogenic growth factor binding properties are maintained. Surprisingly, heparin 2-O-desulfated to not more than 60% of its total uronic units is markedly antiangiogenic.

The desulfation conducted in the conditions described in the present invention also produces the formation of iduronic units with an oxyranic ring in position 2, 3. The opening of the oxyranic ring in the conditions described in the present invention gives rise to L-iduronic or L-galacturonic units.

It is an object of the invention described herein a glycosaminoglycan derivative, particularly desulfated heparin, selectively partially desulfated with a desulfation degree not exceeding 60% of the total uronic units; these sulfation gaps reduce the length of the regular sequences constituted by the succession of disaccharide trisulphate units.

In one particular embodiment, the invention described herein refers to a formula (I) compound

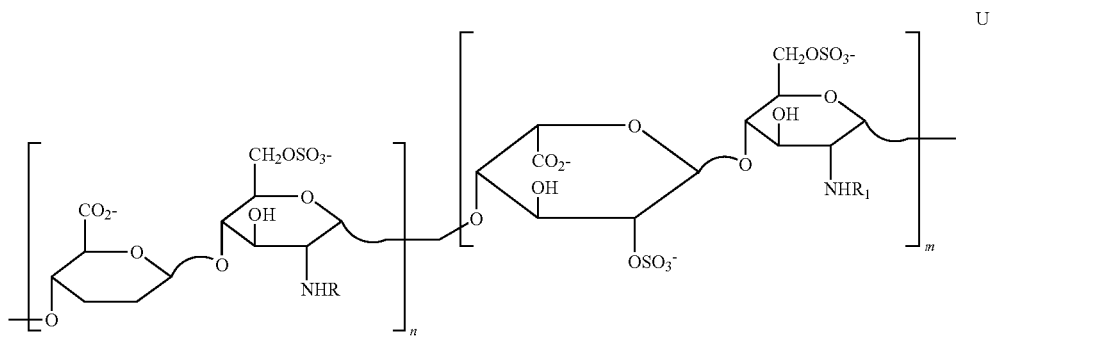

where the U ring may have the following meanings:

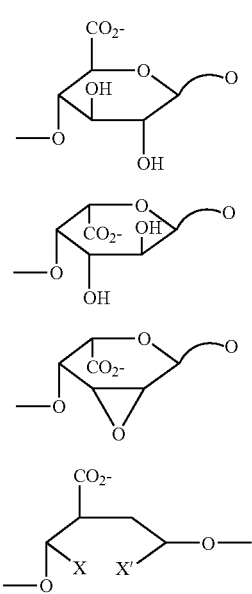

X and X', which can be the same or different, are an aldehyde group or the —CH$_2$-D group, where D is hydroxyl or an amino acid, a peptide or a residue of a carbohydrate or oligosaccharide;

R and R$_1$, which can be the same or different, are an SO$_3$ or acetyl residue;

n and m, which can be the same or different, may vary from 1 to 40; the sum of n+m ranges from 6 to 40; the m:n ratio ranges from 10:2 to 1:1. Preferably, m is greater than or equal to n. Preferably n ranges from 40 to 60% of the sum m+n. The symbol ≴ indicates that the units marked m and n are statistically, distributed along the polysaccharide chain and are not necessarily in sequence.

The compounds which are the subject matter of the invention described herein, have interesting antiangiogenic properties, and are therefore useful as active ingredients for the preparation of medicaments for the treatment of pathologies based on abnormal angiogenesis, and particularly for the treatment of tumors, even more particularly for the treatment of metastases.

Advantageously, the compounds according to the invention present reduced, if not non-existent anticoagulant properties, thus avoiding or reducing the side effects typical of the heparins. A further advantage stems from the fact that the compounds according to the invention can be characterized with instrumental analytical techniques, such as NMR spectroscopy, thus allowing process control which is absolutely desirable from the industrial point of view.

Also in the case of modified heparins, molecular weight (MW) has a very important function when making angiogenesis inhibitors. It is well known, in fact, that a reduction in molecular weight (MW) to values corresponding to pentasaccharide units does not lead to a loss of antiangiogenic activity. On the contrary, it has been established that, beyond a certain length, the heparin chains favor rather than inhibit dimerisation and thus activation of FGF.

DETAILED DESCRIPTION OF THE INVENTION

What is meant by desulfation degree is the percentage of non-sulphated iduronic acids in relation to total uronic acids originally present in the starting heparin. One initial preferred range for the desulfation percentage is from approximately 40 to approximately 60%. Among the formula (I) compounds the preferred compound is:

heparin partially 2-O-desulfated with a molecular weight (MW) of 11200, a polydispersion index D of 1.3, a sulfation degree of 1.99 (expressed as the S03-:COO— molar ratio), a percentage of modified uronic acids compared to total uronic acids of approximately 50% (hereinafter also called ST1514). Said compound is comprised in formula (I) where, among the other corresponding definitions, m:n=1:1 and the units marked m and n are distributed along the polysaccharide chain in a regular, alternating manner.

The compounds according to the invention described herein are prepared by means of a process comprising:

a) basic treatment at a temperature ranging from ambient temperature to approximately 100° C., preferably from 50 to 70° C., and even more preferably at approximately 65° C., which leads to the elimination of a controlled percentage of sulphate groups in position 2 of the iduronic acid and to the formation of epoxide groups; and, if desired b) opening of said epoxide ring at approximately pH 7, at a temperature ranging from approximately 50° C. to approximately 100° C., preferably at approximately 70° C., to yield residues of galacturonic acid; or, alternatively c) opening of said epoxide ring at a temperature ranging from approximately 0° C. to 30° C., preferably at approximately 25° C., to yield residues of iduronic acid; and, if desired d) oxidation of the diols with sodium periodate, to yield the opening of the glycoside ring and the formation of two aldehyde groups per modified residue;

e) reduction of said aldehyde groups to primary alcohol and, if desired, transformation of the D group to a group other than hydroxyl, as envisaged in the different meanings assigned in formula (I)

f) optional acid hydrolysis to obtain oligosaccharides corresponding to the regular sequences, or alternatively g) partial enzymatic hydrolysis with an enzyme selected from the group consisting of lyase, heparinase, heparitinase, or equivalent of products obtained in step e) to yield oligosaccharides, preferably tetra- or octa-saccharides, with the non-reducing terminal residue consisting of unsaturated iduronic acid, the reducing residue consisting of an N sulphoglucosamine and containing at least one residue of open iduronic acid; or, alternatively h) the compound obtained in step a), or the product obtained in step b) is treated by partial enzyme hydrolysis; and, if desired i) subjection of the products obtained in one of steps a), b) and e) to partial 6-O-desulfation; or, alternatively, j) subjection of the starting heparin partially or totally 6-desulfated to steps a), b) and e).

According to the invention described herein, the preferred compound is: heparin partially 2-O-desulfated, obtainable by the process described above, where step a) is conducted for 45 min at 60° C. and step b) at 70° C. at pH 7, and having a molecular weight (MW) of 11200, a polydispersion index D of 1.3, a sulfation degree of 1.99 (expressed as the $SO_3^-$:COO— molar ratio), percentage of modified uronic acids compared to total uronic acids of approximately 50% (hereinafter also called ST1514);

The molecular weights are determined by HPLC-GPC (high performance liquid chromatography–gel permeation chromatography). The sulfation degree is determined by conductimetry and the percentage of modified uronic acids by $^{13}$C-NMR.

MW is the molecular weight, and D is the polydispersion index expressed as MW/Mn.

According to the invention described herein, the starting products are glycosaminoglycans of various origins, preferably naturally occurring heparins. It is also possible to use chemically modified heparins with a percentage content of N,6 disulphate ranging from 0 to 100%. Starting from products with a different 6-O-sulphated glucosamine content, it is possible to modulate the length of the regular sequences between one open iduronic acid and another. The glycosaminoglycans according to the invention that present opening of the glycoside ring are conventionally called RO derivatives by those skilled in the field, meaning by this that the glycoside ring has been opened by means of an oxidation action, followed by a reduction (Reduction-Oxidation —RO). This opening of the glycoside ring is also conventionally called "glycol split", so-called because of the formation of the two primary hydroxy present on the open ring. The compounds referred to herein will also be called "RO" derivatives or "Glycol Split".

In a further embodiment of the invention described herein, the aldehydes and primary hydroxy derived from the opening reaction described above ("glycol split") also lend themselves to the subsequent functionalization. Therefore, formula (I) compounds may also bear equal or different groups, as defined above for X and X', on the primary hydroxy deriving from glycol split. for example, oligosaccharide or peptide groups, ranging from a single saccharide or amino acid to more than one unit of length, preferably 2 or 3 units.

Formula (I) compounds where X and X' are —$CH_2OH$ can also be used as vehicles for other types of drugs, by means of suitable binding with the heparin portion which is capable of providing a stable bond in normal conditions of manufacture and storage of a formulated drug which, however, releases the transported drug in the body, preferably in the vicinity of the target organ. Examples of drugs that can be transported are steroidal and non-steroidal anti-inflammatory drugs, corticosteroids, and other drugs with an antimetastatic action, in which case there will be an advantageous enhancement of the antimetastatic effect as a result of the sum of the separate intrinsic activities of the compounds according to the invention and the antimetastatic agent bound thereto, with the related advantages of a greater target selectivity and lower systemic toxicity. Examples of these drugs are the metalloproteinase inhibitors. Other drugs which can be usefully transported are those that act at the endothelial level. Formula (I) compounds where X and X' are other than hydroxy or aldehyde can also be used as vehicles for drugs, in which case the X and X' groups will act as "spacers" between the transported molecule, that is to say the glycosaminoglycan of the present invention and the molecule acting as the vehicle, in those cases where this may be desirable for reasons of pharmacokinetics or pharmacodynamics.

In the case of compounds according to the invention deriving from heparin, these are prepared starting from heparin itself by means of desulfation techniques known to the technical experts in the field. For example, the desulfation is conducted in the presence of alkaline agents, such as sodium hydroxide, at temperatures ranging from ambient temperature to 100° C., preferably from 50 to 70° C., for example at 60° C., for a sufficiently long period to obtain the desired desulfation. The desulfation is controlled by acting on the process parameters, such as the concentrations of reactants, the temperature and the reaction times. One preferred example consists in maintaining constant concentrations of substrate (glycosaminoglycan) at 80 mg/ml and of NaOH at 1 M, a constant temperature of 60° C. and controlling the desulfation with a reaction time from 15 to 60 min. The expert in the field may vary the conditions, for example by raising the reaction emperature and shortening the reaction time, on the basis of normal trial and error in experimental practice and on the basis of his or her general knowledge of the subject.

The treatment with alkaline agents gives rise to an intermediate product characterized by the presence of an epoxide ring on the desulfated unit. In a thoroughly surprising manner, these intermediates have proved to be endowed with antiangiogenic properties similar to those of the formula (I) compounds. Therefore, a further object of the invention described herein is a derivative of partially desulfated heparin, and therefore heparin with a reduced charge, particularly heparin not de sulfated more than 60%, characterized by an epoxide ring on the desulfation site. Said compounds characterized by an epoxide ring also belong to the objects covered by the present invention, that is to say the pharmaceutical compositions that contain them and their use for the preparation of medicaments with antiangiogenic activity.

The following compounds are preferred:

heparin partially 2-O-desulfated with a molecular weight (MW) of 12900 D, a polydispersion index D of 1.5, a sulfation degree of 2.05 (expressed as the $SO_3^-$:COO— molar ratio), percentage of modified uronic acids compared to total uronic acids: 5% epoxide groups, 29% oxidated and reduced uronic residues (hereinafter also called ST1513);

heparin partially 2-O-desulfated with a molecular weight (MW) of 11000 D, a polydispersion index D of 1.5, a sulfation degree of 2.05 (expressed as the $SO_3^-$:COO— molar ratio), percentage of modified uronic acids compared to total uronic acids: 5% epoxide groups, 29% uronic residues oxidated and reduced uronic residues;

heparin partially 2-O-desulfated with a molecular weight (MW) of 9200 D, a polydispersion index D of 1.5, percentage of modified uronic acids compared to total uronic acids: 11% epoxide groups, 27.5% oxidated and reduced uronic residues.

In one of the possible embodiments of the invention described herein, the following are preferred:

heparin partially 2-O-desulfated, obtainable by the process described above, where step a) is conducted for 15 min at 60° C. and step b) at 70° C. at pH 7, and with a molecular weight of 12900 D, a polydispersion index D of 1.5, a sulfation degree of 2.05 (expressed as the $SO_3^-$:COO— molar ratio), percentage of modified uronic acids compared to total uronic acids: 5% epoxide groups, 29% oxidated and reduced uronic residues (hereinafter called ST1513);

heparin partially 2-O-desulfated, obtainable by the process described above, where step a) is conducted for 30 min at 60° C. and step b) at 70° C. at pH 7 (hereinafter called ST1516), and with a molecular weight (MW) of 11000 D, a polydispersion index D of 1.5, a sulfation degree of 1.8 (expressed as the $SO_3^-$:COO— molar ratio), percentage of modified uronic acids compared to total uronic acids. 5% epoxide groups, 29% oxidated and reduced uronic residues;

heparin partially 2-O-desulfated, obtainable by the process described above, where step a) is conducted for 60 min at 60° C. and step b) at 70° C. at pH 7, and with a molecular weight (MW) of 9200 D, a polydispersion index D of 1.5, percentage of modified uronic acids compared to total uronic acids: 11% epoxide groups, 27.50/0 oxidated and reduced (split) uronic residues (hereinafter called STI515).

Subsequent to the formation of the epoxide ring, the latter is opened, again resorting to known techniques. The percentage of epoxide formed is calculated from the ratio between the areas of the $^{13}$C-NMR signals at approximately 55 ppm, characteristic of carbons 2 and 3 of the uronic acid ring containing the epoxide and the total number of anomeric signals (C1 of the glucosamine and uronic acid residues). If the opening is conducted hot, a galacturonic acid residue is obtained, whereas, if the opening of the epoxide ring is conducted cold, an iduronic acid residue is obtained. Preferred examples of compounds containing an epoxide ring are those obtainable by the process described above and having epoxidated uronic acid contents of 14% (hereinafter STI509), 24% (hereinafter STI525) and 30% (hereinafter STI526), respectively.

The partially desulfated heparin is then subjected to "glycol-split" (RO for short), according to the process defined above and Smith degradation (SD for short).

Alternatively, formula (I) compounds can also be obtained without passing via the epoxide intermediate, that is to say by direct glycol split and subsequent Smith degradation.

The process described so far leads to formula (I) compounds in which the X and X' groups are both —$CH_2OH$.

For X and X' other than —$CH_2OH$, methods are available to the expert in the field for transforming the hydroxyl group with other groups envisaged in the definitions given above. For example, the conjugation with amino acids or peptides can be done by treating the intermediate aldehyde derived from the glycol-split reaction with a reductive amination reaction (Hoffmann J. et al. Carbohydrate Research, 117, 328-331 (1983)), which can be conducted in aqueous solvent and is compatible with maintenance of the heparin structure.

If desired, and this constitutes a further object of the invention described herein, the formula (I) compounds can be further degraded with acid agents in suitable pH conditions, e.g. at pH 4, to yield a mixture of oligo saccharides that maintain the antiangiogenic properties.

In the same way, objects of the present invention are the compounds obtained by one of the steps g), h), i) and j) of the process described above.

Objects of the invention described herein are pharmaceutical compositions containing as their active ingredient at least one formula (I) compound, alone or in combination with one or more formula (I) compounds, or, said formula (I) compound or compounds in combination with the desulfated heparins described above, e.g. the epoxidated intermediates; the latter can also be used alone as active ingredients in the pharmaceutical compositions. The active ingredient according to the present invention will be in a mixture with suitable vehicles and/or excipients commonly used in pharmaceutical technology, such as, for instance, those described in "Remington's 10 Pharmaceutical Sciences Handbook", latest edition. The compositions according to the present invention will contain a therapeutically effective quantity of the active ingredient. The doses will be determined by the expert in the field, e.g. the clinician or primary care physician according to the type of disease to be treated and the patient's condition, or concomitantly with the administration of other active ingredients. By way of an example, doses ranging from 0.1 to 100 mg/kg may be indicated.

Examples of pharmaceutical compositions are those that can be administered orally or parenterally, intravenously, intramuscularly, subcutaneously, transdermally or in the form of nasal or oral sprays. Pharmaceutical compositions suitable for the purpose are tablets, hard or soft capsules, powders, solutions, suspensions, syrups, and solid forms for extemporary liquid preparations. Compositions for parenteral administration are, for example, all the intramuscular, intravenous and subcutaneous injectable forms as well as solutions, suspensions and emulsions. Liposome formulations should also be mentioned. The tablets also include forms for the controlled release of the active ingredient whether as oral administration forms, tablets coated with suitable layers, microencapsulated powders, complexes with cyclodextrins, depot forms, for example, subcutaneous forms, such as depot injections or implants.

The compounds according to the invention described herein possess antiangiogenic activity. This makes them suitable for the preparation of medicaments useful for the treatment of objects, generally mammals, and particularly human subjects, suffering from altered angiogenesis. Examples of diseases treated with the medicament which is the object of the present invention are primary tumors, metastases, diabetic retinopathies, psoriasis, retrolenticular fibroplasia, restenosis after angioplasty and coronary by-pass.

Advantageously, the compounds according to the present invention are substantially devoid of the side effects typical of heparin. In particular, the compounds according to the invention are substantially devoid of anticoagulant activity. By substantially devoid of such activity the expert in the field means no or only negligible activity from the point of view of clinical use.

One of the first growth factors found to have an angiogenic role was bFGF (or FGF-2) followed shortly afterwards by aFGF (or FGF-1) (for a review of the subject see Christofori, Oxford University, 1996). Both proteins are members of a class of growth factors characterized by a high degree of affinity for heparin. Other potent angiogenic inductors are VEGF, VEGF-B and VEGF-C. All three VEGF factors, like the two FGFs, are expressed ubiquitously in the body. Both of these types of factors, a/bFGF (FGF-1 and FGF-2) and VEGF, bind to specific high-affinity receptors with a transmembrane domain possessing tyrosine-kinase activity. The three receptors for the VEGFs-VEGF-1 (flt-1), VEGF-2 (kdr/flk-1) and VEGF-3 (flt-4) are expressed specifically on endothelial cells, whereas the four FGF receptors are expressed in numerous organs and tissues (for a review of the subject see Risau and Flame 1995 Annu. Rev. Cell Dev: Biol. 11: 73-91). bFGF binding to heparin or to fragments of heparan sulphate causes their dimerisation and the possibility of binding to their own receptor by activating the transduction pathway of the signal that activates the endothelial cell in both mitogenesis and differentiation.

The inhibition of FGF binding to heparin or to fragments of heparan sulphate thus represents a valid therapeutic target in combating the pathological neoangiogenesis induced by an increased local or systemic level of growth factors.

To this end an in-vitro model was designed capable of assessing the interference of the various different heparin derivatives with bFGF binding to its own receptor.

In particular, ovarian cells of Chinese hamsters (CHO) were used which possess heparan sulphates on their surface, but lack FGF receptor 1 for the FGF called CHO—K1. CHO cells called CHO-745flg were also used, which express the FGF receptor 1 but which, unlike the former group, do not possess membrane heparan sulphates. These latter cells were stably transfected with cDNA for green fluorescent protein and for this reason could be observed under the fluorescence microscope with a combination of filters for the detection of green emission. In brief, the technique is based on the possibility that the two types of cells may interact (form stable bonds) only if FGF is added to the two cell types. In fact, in this case, the heparan sulphates of the CHO-745flg cells will bind to FGF, which in turn will bind to the CHO-K1 cells, establishing a bridge. The binding that occurs is detectable as a result of the green fluorescence emitted by the CHO-745flg cells.

In addition, the compounds were assayed for their cell proliferation inhibiting activity. In fact, one of the main effects of FGF is to stimulate cell growth in the absence of serum in cells expressing FGF receptor 1 (FGFR-1).

To this end, two cell lines were used, both expressing FGFR-1 (L6WT1 and bovine aorta cells), the growth of which was evaluated in the presence of FGF with or without the addition of heparin derivatives for which an inhibitory activity was expected.

Inhibition of FGF2-mediated Intercellular Adhesion

CHO-K1 cells were seeded at a density of 90,000 cells/cm2 in 24-well plates. After 24 hours the cells were fixed in 3% glutaraldehyde in PBS for 2 hours at 4° C. and washed with 0.1 M glycine/PBS. On the fixed monolayers CHO 745/flg cells, transfected with FGFR-1, at a density of 50,000 cells/cm2 in DMEM containing 10 mM EDTA, 30 ng/ml FGF-2 and increasing doses of the test compounds. After 2 hours' incubation at 37° C., the adhering cells were counted under the inverted microscope. The results were expressed as percentage of the number of cells adhering compared to those measured in the absence of the test compounds. The compounds were examined in triplicate at 6 concentrations ranging from 1 ng/ml to 100 μg/ml and the $ID_{50}$ was calculated for each compound (Table 1).

TABLE 1

Inhibition of intercellular adhesion (ID50) of CHO-K1 e CHO- 745flg cells

| Product | Inhibition ($ID_{50}$) |
|---|---|
| Heparin | 100 |
| RO heparin | 8 |
| ST1513 | 80 |
| ST1516 | 110 |
| ST1514 | 105 |
| ST1515 | 120 |
| ST1525 | 50 |
| ST1528 | 75 |
| ST1507 | 125 |

Inhibition of DNA Synthesis in L6 Cells Transfected with FGFR-1

L6-WT1 cells (rat myoblasts transfected with FGFR-1) were seeded at a density of 25,000 cells/cm$^2$ in 48-well plates in DMEM+10% FCS. After 24 hours the cells were washed with serum-free medium and incubated for 48 hours with DMEM+0.5% FCS. The cells were then incubated for 16 hours with FGF-2 at the concentrations of 15 and 30 ng/ml in the presence or absence of the test compounds (all at 100 μg/ml). At the end of the incubation 3H-thymidine (0.25 μCi/well) was added without changing the medium. After 6 hours, precipitable TCA was measured. Each experimental point is the mean of 3 determinations. The results are given in Table 2.

TABLE 2

Inhibition of DNA synthesis in L6 cells transfected with FGFR-1.

| Product | Incorporation of 3H-thymidine (% vs. control) |
|---|---|
| Heparin (FGF-2 15 ng/ml) | 50 |
| Heparin (FGF-2 30 ng/ml) | 74 |
| Heparin RO (FGF-2 15 ng/ml) | 41 |
| Heparin RO (FGF-2 30 ng/ml) | 80 |
| ST1513 (FGF-2 15 ng/ml) | 93 |
| ST1513 (FGF-2 30 ng/ml) | 102 |
| G3025B (FGF-2 15 ng/ml) | 68 |
| G3025B (FGF-2 30 ng/ml) | 71 |
| ST1514 (FGF-2 15 ng/ml) | 58 |
| ST1514 (FGF-2 30 ng/ml) | 99 |
| ST1515 (FGF-2 15 ng/ml) | 79 |
| ST1515 (FGF-2 30 ng/ml) | 100 |

Effect on DNA Synthesis in Bovine Aorta Endothelial Cells (BAEC)

BAEC cells were seeded at a density of 2,500 cells/cm$^2$ in 48-well plates in EGM Bullet Kit complete medium. After 24 hours the cells were cultivated in the absence of serum in EGM medium without bovine brain extract and hEGF. After a further 24 hours, the cells were treated with 30 ng/ml of bFGF in the presence of increasing concentrations of the test compound. After 16 hours, 1 μCi/ml of 3H-thymidine was added to the medium. After 6 hours, precipitable TCA activity was measured. Each experimental point is the mean of 8 determinations. The results are given in Tables 3-6.

TABLE 3

Effect on DNA synthesis in bovine aorta endothelial cells (BAEC) - ST1514

| Concentration ng/ml | Incorporation of $^3$H-thymidine (% vs control) |
|---|---|
| 1 | 80 |
| 10 | 78 |
| 100 | 42 |
| 1000 | 33 |
| 10000 | 22 |
| 100000 | 5 |

TABLE 4

Effect on DNA synthesis in bovine aorta endothelial cells (BAEC) - ST1528

| Concentration ng/ml | Incorporation of $^3$H-thymidine (% vs control) |
|---|---|
| 1 | 85 |
| 10 | 73 |
| 100 | 85 |
| 1000 | 32 |
| 10000 | 28 |
| 100000 | 5 |

TABLE 5

Effect on DNA synthesis in bovine aorta endothelial cells (BAEC) - ST1525

| Concentration ng/ml | Incorporation of $^3$H-thymidine (% vs control) |
|---|---|
| 1 | 75 |
| 10 | 67 |
| 100 | 26 |
| 1000 | 21 |
| 10000 | 7 |
| 100000 | 2 |

TABLE 6

Effect on DNA synthesis in bovine aorta endothelial cells (BAEC) - ST1507

| Concentration ng/ml | Incorporation of $^3$H-thymidine (% vs control) |
|---|---|
| 1 | 92 |
| 10 | 92 |
| 100 | 45 |
| 1000 | 40 |
| 10000 | 18 |
| 100000 | 12 |

Test of Cell Proliferation in BAEC

BAEC cells at the 7th pass were seeded at a density of 2,500 cells/cm$^2$ in 96-well plates in EBM medium without bovine brain extract and hEGF. To this medium were added 30 ng/ml of FGF-2 and each of the test compounds at 5 concentrations ranging from 10 ng/ml to 100 μ/ml. After 3 days the cells were fixed and stained with crystalviolet and the optical density was determined by means of an ELISA microplate reader. Each experimental point was done in quadruplicate and the ID50 was calculated. The results are given in Table 7.

TABLE 7

Test of cell proliferation in BAEC

| Product | Inhibition (ID$_{50}$) μg/ml |
|---|---|
| Heparin | 100 |
| ST1509 | 0.02 |
| ST1525 | 10 |
| ST1526 | 0.02 |
| ST1527 | 100 |
| ST1528 | 0.1 |

Test of Cell Proliferation in Foetal BAEC GM 7373

GM7373 cells were seeded at a density of 70,000 cells/cm$^2$ in 96-well plates in MEM+10% FCS medium. After 24 hours, the cells were washed with serum-free medium and treated with 10 ng/ml of FGF-2 in medium containing 0.4% FCS. After 8 hours, the test compounds were added to the medium at 5 concentrations ranging from 10 ng/ml to 100 μg/ml. After a further 16 hours, the cells were trypsinised and counted in a Burker chamber. The ID$_{50}$ was calculated for each compound and the results are the means of 2 experiments in triplicate. The results are given in Table 8.

TABLE 8

Test of cell proliferation in foetal BAEC GM 7373

| Product | Inhibition (ID$_{50}$) μg/ml |
|---|---|
| Heparin | 2 |
| ST1509 | 0.3 |
| ST1525 | 2 |
| ST1526 | 1 |
| ST1527 | 20 |
| ST1528 | 0.2 |
| ST1514 | 0.1 |

Inhibition of Angiogenesis

For the study of angiogenesis the model used was the chick embryo chorioallantoic membrane model (Ribatti e al. Int. J. Dev. Biol., 40, 1189 (1996)).

300 embryonated hens' eggs were incubated at 37° C. in constant humidity conditions. On the 3rd day of incubation, after aspirating 2-3 ml of albumen from the acute pole of the egg so as to detach the CAM from the shell, a window was cut with scissors in the shell. The vessels underlying the CAM were thus exposed. The window was closed with a transparent glass panel and the eggs were put back into the incubator. On the 8th day of incubation, in sterile conditions, the CAMs were treated according to the protocol described below using a technique developed recently (Ribatti et al. J. Vasco Res. 34, 455 (1997)), which involves the use of sterile gelatin sponges measuring 1 mm2 in size. Each molecule was resuspended in 3 μl of PBS at a concentration of 50 or 100 μg/embryo. As a positive control, FGF-2 was used (1 μg/sponge), for which potent angiogenic activity on the CAM has been demonstrated (Ribatti et al., Dev. Biol. 170, 39, (1995)). The sponges were first rested on the surface of the CAM, and then 3 μl of solution of the test substance were pipetted onto the surface of the sponge. The CAMs were examined daily using a Zeiss SR stereomicroscope equipped with a photographic device. The experiments were discontinued on the 12th day of incubation, when an overall assessment of the angiogenic activity of the molecules was carried out, expressed as percentage inhibition in relation to the number of experiments initiated and completed (Table 9). In addition, for compound ST1514, assayed at the concentration of 100 μg/embryo, a macroscopic quantitative evaluation of the angiostatic activity was also carried out according to the technique proposed by Brooks et al. (Science, 264, 569, (1994)), counting the number of vessels surrounding the sponge. The number of vessels was compared with that of the control sponges treated with PBS (vehicle of the test compound) and with FGF-2 (positive control). The results are given in Table 10.

TABLE 9

Angiostatic activity on CAM model

| Compound | Concentration (μg/embryo) | N. experiments | Inhibition (%) |
|---|---|---|---|
| N-acetylated heparin | 50 | 10 | 0 |
| RO heparin (ox-red 19.6%) | 50 | 10 | 20 |
| ST1514 (RO 56%) | 50 | 10 | 50 |
| ST1514 (RO 56%) | 100 | 10 | 80 |

It should be noted that naturally occurring heparin has no activity.

TABLE 10

Angiostatic activity: macroscopic quantitative evaluation (Brooks)

| Compound | N. embryos | N. vessels at sponge/CAM interface |
|---|---|---|
| ST1514 (100 μg/embryo) | 10 | 2 + 1 |
| PBS (3 μl) | 5 | 7 + 2 |
| FGF-2 (1 μg/embryo) | 5 | 50 + 4 |

It should be noted that naturally occurring heparin has no activity.

Evaluation of Heparin Toxicity in Balb/c Mice.

20 6-week-old female Balb/c mice weighing 20 g (Harlan), divided into groups by casual randomisation, were treated with heparin sodium, as a reference, and with the compound according to the present invention called STI514. The treatment schedule was of the q2dx5 type, i.e. 5 total administrations at intervals of 2 days, administering 200 μl/mouse of 50 mg/kg/10 ml and 25 mg/kg/10 ml solutions subcutaneously. The substances were solubilized as follows:

Heparin sodium: the solution is prepared by solubilizing 160 mg of powder in 4 ml of PBS 1× pH 7.4 free of $Ca^{++}$-and $Mg^{++}$-ions; it is subdivided into aliquots of 243 μl and stored at −20° C. At the time of treatment, the solution is diluted in $Ca^{++}$-and $Mg^{++}$-free PBS (Dulbecco, modified formula) 1×, pH 7.4 so as to have the substance at final concentrations of 50 mg/kg/10 ml and 25 mg/kg/10 ml.

ST1514: the solution is prepared by solubilizing 160 mg of powder in 4 ml of $Ca^{++}$-and $Mg^{++}$-free PBS 1×, pH 7.4; it is subdivided into aliquots of 243 μl and stored at −20° C. At the time of treatmen, the solution is diluted in $Ca^{++}$-and $Mg^{++}$-free PBS (Dulbecco, modified formula) 1×, pH 7.4 so as to have the substance at final concentrations of 50 mg/kg/10 ml and 25 mg/kg/10 ml.

48 hours after the last administration of the test substances a blood sample is taken for full blood count and haematological analysis.

Blood sampling: the mice are placed in a hermetically sealed box, into which is insufflated $CO_2$ in an amount sufficient to stun the animal. Blood is then taken from the retro-orbital plexus of each animal (approximately 1 ml of blood/mouse) which is distributed in amounts of 0.4 ml of blood/mouse in Eppendorf test tubes containing 20 μl of Vister heparin (5000 U/ml) for carrying out the full blood count and haematological analysis; and the same amount of blood is distributed in other Eppendorf test tubes containing 50 μl of 3.8% sodium citrate in order to perform prothrombin time determinations. After taking the blood sample, each animal is sacrificed by cervical dislocation.

Number of samples: 2 blood samples/mouse are taken, with which two full blood counts are carried out and two slides and a plasma sample are produced to be stored at −20° C.

Full blood count: the appliance (Cell Analyzer 580 A, DELCON) is used according to the standard procedure described in the operating manual. The blood sample (25 μl) is taken by the dilutor and brought up to a volume of 10 ml (dil. 1:400) with isotonic solution (PLTA saline, DELCON). From this solution (called solution A), the dilutor automatically takes a sample of 100 μl and brings it up to a volume of 10 ml (dil. 1:100), thus obtaining solution B. To solution A are added 3 drops of Emosol (DELCON) for lysis of the red blood cells. This solution is used for the WBC reading. Solution B, on the other hand, is used for the RBC and platelet (PLT) readings. Each sample is read in duplicate.

The data obtained will be analyzed using ANOVA.

The groups of animals treated with heparin sodium at the doses of 50 mg/kg/10 ml and 25 mg/kg/10 ml present a marked haematoma at the inoculum site; this phenomenon does not occur in the groups submitted to treatment with ST1514. Autopsies conducted in the study animals reveal that the groups submitted to treatment with heparin sodium at doses of 50 mg/kg/10 ml and 25 mg/kg/10 ml present livers with abnormal characteristics, whereas no such phenomenon is detected in the groups treated with ST1514.

The data relating to the haematological analysis show a reduction in red blood cells in both groups treated with heparin sodium at the doses of 50 mg/kg and 25 mg/kg as compared to the control group, whereas no such difference is detectable in the groups treated with ST1514.

The group treated with heparin sodium at the dose of 25 mg/kg presents a significant platelet deficiency compared to the control group. None of the study treatment groups presents significant differences in the numbers of white blood cells as compared to the control group.

The following examples further illustrate the invention.

EXAMPLE 1

1 g of heparin is dissolved in 12.5 ml of NaOH 1N. The solution is heated and stirred at 60° C. for 45 minutes. The reaction is blocked by rapid cooling and neutralization. The solution is then heated at 70° C. at pH 7 until the epoxide ring is completely open (the reaction trend is controlled by NMR). The desulfated sample (here called G2999H) is dissolved in 20 ml of water and cooled to 4° C. After the addition of 20 ml of a solution of $NaIO_4$ 0.2 M, the solution is left to stir in the dark for 20 hours, and the reaction is stopped by adding ethylene glycol and 48 the salts are eliminated by tangential ultrafiltration. 400 mg of $NaBH_4$, subdivided into several portions, are added to the desalted solution (30-40 ml). The solution is left to stir for 3 hours at ambient temperature, then neutralized with diluted HCl and desalted by tangential ultrafiltration. 710 mg of product, here called ST1514, are obtained.

Molecular weight (MW): 11200 D, polydispersion index D 1.3, sulfation degree 1.9 (expressed as $SO_3^-$:COO— molar ratio); the percentage of modified uronic acids compared to total uronic acids is approximately 50%. The compound was characterized by means of NMR spectroscopy (FIG. 1).

EXAMPLES 2-4

Adopting the same procedure as in example 1, with the exception that the basic solution was heated for 15, 30 and 60 minutes, respectively, compounds with the following characteristics were obtained:

ST1513: molecular weight (MW) 12900 D, polydispersion index D 1.5, sulfation degree 2.05 (expressed as $SO_3^-$:COO— molar ratio), percentage of modified uronic acids compared to total uronic acids: 5% epoxide groups, 29% oxidated and reduced (split) uronic residues;

ST1516: molecular weight (MW) 12900 D, polydispersion index D 1.5, sulfation degree 1.8 (expressed as $SO_3^-$:COO— molar ratio), percentage of modified uronic acids compared to total uronic acids: 5% epoxide groups, 29% oxidated and reduced (split) uronic residues;

ST1515: molecular weight (MW) 9200 D, polydispersion index D 1.5, percentage of modified uronic acids compared to total uronic acids: 11% epoxide groups, 27.5% oxidated and reduced (split) uronic residues.

EXAMPLE 5

Glycol-split N-acetyl heparins (NA-Hgs)

Fully N-acetylated heparin ($^{100}$NA-H,) was prepared from H (Heparin) as described. (Inohue, Y., Nagasawa, K. Selective N-desuljation of heparin with dimethylsulphoxide containing water or methanol. Carbohydr. Res. 1976, 46, 87-95.) 50% N-acetyl-heparin ($^{50}$NA-H,) was prepared by solvolytic partial N-desulfation of H in DMSO/MeOH (9/1, v/v) (Nagasawa, K.; Inoue, Y.; Kamata. T. Solvolytic desuljation of glycosaminoglycuronan sUljates with dimethyl sulphoxide containing water or methanol. Carbohydr. Res. 1977, 58, 47-55.) for 120 min at 20° C., followed by N-acetylation with acetic anhydride in alkaline medium. (Inohue. Y., Nagasawa, K. Selective N-desuljation of heparin with dimethylsulphoxide containing water or methanol. Carbohydr. Res. 1976, 46, 87-95.) The N-acetylation degree was determined by integration of $^{13}$C NMR signals at 60 and 55 ppm corresponding to the C-2 of $GlcNSO_3$ and GlcNAc, respectively. The glycol-split derivative of $^{50}$NA-H ($^{50}$NA-H-$^{25}$gs,) ST1518 (N-Ac), was obtained from $^{50}$NA-H (1 g) dissolved in 50 mL of 0.1 M $NaIO_4$. The solution was stirred at 4° C. for 16 h in the dark. The reaction was stopped adding 5 mL ethyleneglycol and the solution was dialyzed. Solid sodium borohydride (500 mg) was added to the retentate solution under stirring in several portions. After 2-3 h the pH was adjusted to 3 with 0.1M HCl, and the solution was neutralized with 0.1M NaOH. After dialysis, $^{50}$NA-H-$^{25}$gs was recovered in a 46% yield by freeze drying.

EXAMPLE 6

LMW-derivatives of $H^{46}$gs ST2184 (LMW-denvative of Sf1514) were prepared by nitrous acid depolymerization. A solution of polysaccharide (4 g) were dissolved in 65 mL $H_2O$ was cooled at 4° C. then added of 75 mg of $NaNO_2$ and the pH was adjusted to 2 with 0.1 M HCl. The solution was stirred at 4° C. for 20 min and then the pH was brought to 7. Solid $NaBH_4$ (1 g) was added in several portions under stirring. After 2-3 h the pH was adjusted to 4 with 0.1 M HCl and the solution was neutralized with 0.1 M NaOH. The product, obtained by precipitation with 3 volumes of ethanol, was dissolved in water and recovered by freeze-drying. The extent of glycol-splitting percentage expressed as glycol split residues referred to total uronic acids was evaluated by integration of the $^{13}$C NMR signals at 106.5 ppm and 102 ppm corresponding to C 1 of the split uronic residues and 2-O-sulfated iduronic residues, respectively. The depolymerization degree (DP) was evaluated by integration of the $^{13}$C NMR signals at 98-107 ppm and 82, 85 and 87 ppm, corresponding to total C1 and C2, C3 and C5 of the anhydromannitol unit, respectively.

To evaluate the effect of substituents at the level of glycol split residues, the 74% glycol-split heparin derivative Odes-ulfated heparin in galacturonic form H-$^{42}$GalA was converted into its glycine and taurine derivatives: (H-$^{74}$gs/G, and H-$^{74}$gs/T).

EXAMPLE 7

Glycine (H-$^{74}$gs/G) ST1829, Taurine (H-$^{74}$gs/T) ST1828 and Ammonium ST1919 Derivatives of Glycol-Split Heparins These derivatives were obtained by reductive amination (Hoffman. J.; Larm. O.; Scholander. E. A new method for covalent coupling of heparin and other glycosaminoglycans to substances containing primary amino groups. Carbohydr. Res. 1983. 11 7. 328-331.) of polydialdehydes obtained by periodate oxidation of GalA analogs. All the derivatives were prepared from the GalA containing intermediate also used for preparation of H-$^{74}$gs. To prepare the glycine derivative H-$^{74}$gs/G, H-$^{42}$GalA (300 mg) was dissolved in 7.5 mL of $H_2O$, then added of 7.5 mL 0.2M $NaIO_4$ solution. After stirring at 4° C. for 16 h in the dark, the reaction was stopped adding 1 mL ethyleneglycol and the solution was dialyzed for 16 h. The solution volume (about 100 mL) was reduced to 12 mL under vacuum, then glycine (1.6 g) was added under stirring in several portions. After 1 h solid $NaBH_4$ (200 mg) was added in several portions under stirring and the pH was adjusted to 6 with 0.1M HCl. After 3 h the pH was adjusted to 4 with 0.1M HCl, and the solution was neutralized with 0.1M NaOH. After desalting (which removed also unreacted glycine), the final product ST1829 was recovered in a 85% yield by freeze drying. Typical $^{13}$C NMR signals: 52 ppm (NH $CH_2CO_2$): 106.5 ppm (C1 of glycol-split uronic acid residues). The extent of glycol-splitting (74%) was evaluated as described before for glycol-split heparins. The glycine molar substitution G % (48%, as referred to total split uronic acids) was evaluated from the area of $^{13}$C NMR signals at 52 ppm (A) and 106.5 ppm (B), corresponding to CH2 glycine signals and split uronic residues, respectively, as follows: G %=A/B×100.

The amine derivative H-$^{74}$gS/A (ST1919) was prepared following the same procedure described for H-$^{74}$gs/G, using $NH_4OH$ instead of glycine (yield: 57%).

The compounds of Examples 5-7 are summarized by the following formula:

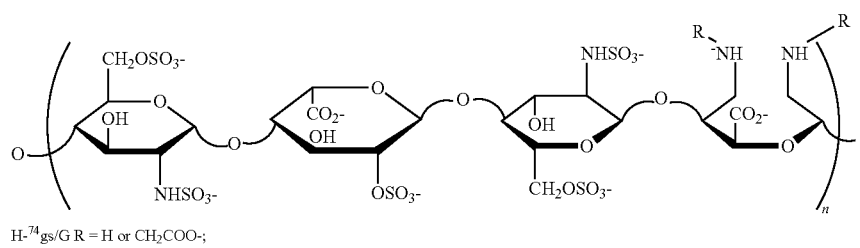

H-$^{74}$gs/G R = H or CH$_2$COO-;
H-$^{74}$gs/T R = H or CH$_2$CH$_2$SO$_3$-
(n = 10)

In the FGF2-mediated cell-cell adhesion test, FGF2 causes cell-cell attachment by linking FGFRs carried on FGFR1-overexpressing HSPG-deficient CHO mutants to HSPGs expressed by neighboring wildtype CHO-K1 cells. 25 In this assay the glycine derivative ST1829 (H-74gs/G) prevent the formation of the FGFR/FGF2/HSPG ternarycomplex with a potency (ID50=10-30 ng/mL) Similar or better than that shown by heparin (ID50=100 ng/mL).

MeWo melanoma cells (5×105) were inoculated i.d. Animals were treated s.c. twice a day with 25 mg/kg ST2184 for ten days. Mice were sacrificed and the skin areas in contact with the dorsal side of the chamber were trimmed off. Quantification of the total vascularized area was performed by computer-assisted image analysis.

The following Table 12 shows the results.

TABLE 11

Average Molecular Weight (Mw and pd)[1], Sulfation Degree (DS)[2], Inhibition of FGF2-mediated Cell-Cell Adhesion[3] and Endothelial Cell proliferation,[3] and Antiangiogenic Activity in CAM Assay[4,5] for Heparin and Heparin Derivatives.[a]

| | Mw | (Pd) | DS | Cell-Cell Adh. (ID$_{50}$, ng/mL) | Cell Prolif. (ID$_{50}$, ng/mL) | CAM (% inhibition)[b] | CAM vs FGF-2 (% inhibition)[b] | CAM vs VEGF[5] (% inhibition)[c] |
|---|---|---|---|---|---|---|---|---|
| Heparin (H) | 15 800 | (1.1) | 2.2 | 100 | 2 000 | 0 | | |
| *2-O-desulfated heparins* | | | | | | | | |
| H-$^{42}$GalA (Starting Material of H$^{74}$-GS) | 13 200 | (1.2) | 1.8 | 300 | 1 000 | nd | | |
| *Glycol-split heparins* | | | | | | | | |
| H-$^{46}$gs ST1514 | 11 900 | (1.2) | 1.7 | 100 | 300 | 80 | 70 | 50 |
| H-$^{74}$gs ST1827 | 12 800 | (1.3) | 1.5 | 10 | 100 | 60 | | |
| LMW-H-$^{52}$gs ST2184 | 5 800 | (1.4) | 1.7 | 30 | 300 | 70 | | 70 |
| vLMW-H-$^{52}$gs ST2010 | 3 000 | (2.2) | 1.7 | 30 | 300 | 90 | | |
| *Derivatives of glycol-split heparins* | | | | | | | | |
| H-$^{74}$gs/G ST1829 | ~12.000 | nd | nd | 10 | 3 000 | 80 | | |
| H-$^{74}$gs/T ST1828 | ~.12.000 | nd | nd | 300 | 1 000 | 70 | | |
| *N-acetylated heparins* | | | | | | | | |
| $^{100}$NA-H ST1511 | 11 300 | (1.3) | 1.5 | 30 000 | >100 000 | 0 | 55 | 40 |
| $^{50}$NA-H ST1512 | 10 900 | (1.3) | 1.8 | 3 000 | 1 000 | 0 | | |
| $^{50}$NA-H-$^{25}$gs ST1318 | 12 100 | (1.3) | 1.7 | 300 | 30 000 | 30 | 30 | 30 |

[a] Percent conversions are indicated as superscripts on symbols of products;
[b] 100 μg/embryo; nd.;
[c] VEGF 500 ng/embryo: not determined
[1] Casu, B.; Gennaro, U. A simple conductimetric method for determining the sulfate and carboxylate groups in heparins and chondroitin sulfates. *Carbohydr. Res.* 1975, 39, 168-176.
[2] Keary, C M. Charaterization of Methocel cellulose ethers by aqueous SEC with multiple detectors. *Carbohydr. Polymers* 2001, 45, 293-303.
[3] Leali, D.; Belleri, M; Urbinati, C; Coltrini, D.; Oreste, P.; wppelti, G.; Ribatti, D.; Rusnati, M.; Presta, M. Fibroblast growth factor-2 antagonist activity and angiostatic capacity of sulfated *Escherichia coli* K5 polysaccharide derivatives. *J. Biol. Chem.* 2001, 276, 37900-37908.
[4] Ribatti, D.; Goulandris, A.; Bastaki, M.; Vacca, A.; Iurlaro, M.; ROllcali, L; Presta, M. New model of angiogenesis and alltiallgiogellesis ill the chick embryo chorioallantoi membralle: the gelatill spollgelchorioallalltoic membrane assay. *J. Vasc. Res.* 1997, 34, 455-463.
[5] Ulldersulfated, low lll0leeuiar weight glycol-split heparin as an antiangiogellie VEGF antagonist. Pisano C, Aulicino C, Vesci L, Casu B, Naggi A, Torri G, Ribatti D, Belleri M, Rusnati M, Presta M. *Glycobiology.* 2004 Oct. 20.

TABLE 12

| Effect of ST2184 on vascularization of MeWo melanoma xenografted onto nude mice. | | | |
|---|---|---|---|
| Treatment | Daily Dose (mg/kg) | n | Vascularized area $mm_2 \pm SE$ |
| Vehicle | / | 10 | $8.9 \pm 0.4$ |
| ST2184 | 50 | 10 | ***$5.2 \pm 0.5$ |

***$P < 0.001$ vs vehicle (Mann-Whitney).

What is claimed is:

1. A method of inhibiting angiogenesis, comprising administering to a subject suffering from abnormal angiogenesis a 2-O-desulfated glycosaminoglycan derivative with a iduronic acid desulfation degree not greater than 60% of the total uronic units, which has the following formula (I):

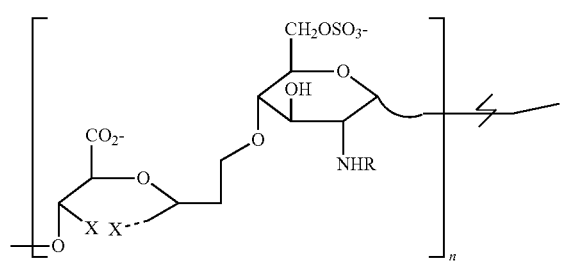

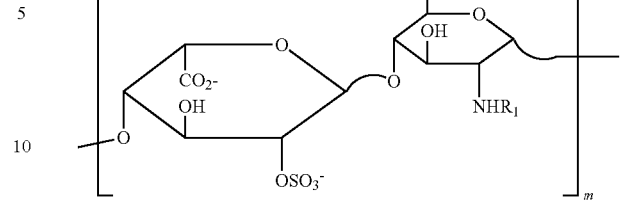

where X and X' are —$CH_2$-D group, where D is selected from the group consisting of hydroxyl, amino acid, $NH_2$, $HN(CH_2)_2SO_3Na$;

R and R1, which are the same or different, are an $SO_3$ or acetyl residue;

n and m, which are the same or different, vary from 1 to 40;

the sum of n+m ranges from 6 to 40;

the m:n ratio ranges from 10:2 to 1:1, and the symbol ⌇ indicates that the units marked m and n are statistically distributed along the polysaccharide chain and are not necessarily in sequence.

2. The method of claim 1, wherein said derivative is a modified heparin being subjected to partial N-desulfation.

3. A method of inhibiting angiogenesis, comprising administering to a subject suffering from abnormal angiogenesis a 2-O-desulfated glycosaminoglycan derivative with a iduronic acid desulfation degree not greater than 60% of the total uronic units, which has the following formula:

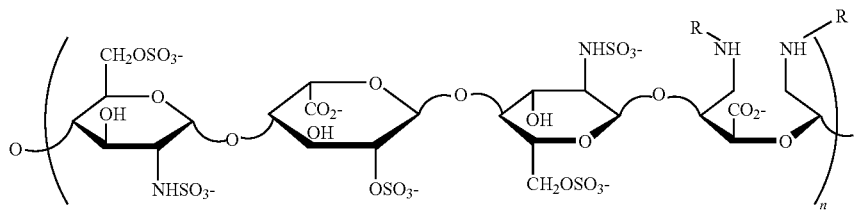

where R are different and are H or $CH_2COO^-$ and where n is 10.

4. A method of inhibiting angiogenesis, comprising administering to a subject suffering from abnormal angiogenesis a 2-O-desulfated glycosaminoglycan derivative with a iduronic acid desulfation degree not greater than 60% of the total uronic units, which has the following formula:

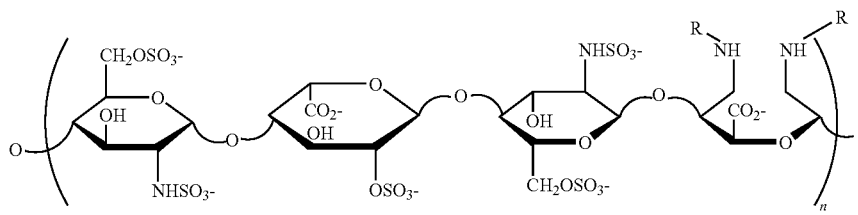

where R are different and are H or $CH_2CH_2SO_3^-$ and n is 10.

5. A method of treating a pathological state due to abnormal angiogenesis, comprising administering to a subject suffering from abnormal angiogenesis a 2-O-desulfated glycosaminoglycan derivative with a iduronic acid desulfation degree not greater than 60% of the total uronic units, which has the following formula (I):

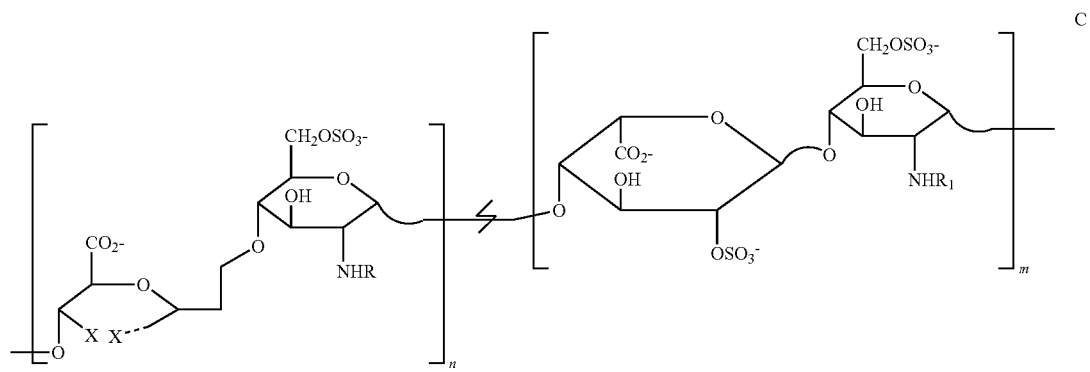

where X and X' are —$CH_2$-D group, where D is selected from the group consisting of hydroxyl, amino acid, $NH_2$, $HN(CH_2)_2SO_3Na$;

R and R1, which are the same or different, are an $SO_3$ or acetyl residue;

n and m, which are the same or different, vary from 1 to 40; the sum of n+m ranges from 6 to 40;

the m:n ratio ranges from 10:2 to 1:1, and the symbol ⌇ indicates that the units marked m and n are statistically distributed along the polysaccharide chain and are not necessarily in sequence.

6. The method of claim 5, wherein said derivative is a modified heparin being subjected to partial N-desulfation.

7. A method of treating a pathological state due to abnormal angiogenesis comprising administering to a subject suffering from abnormal angiogenesis a 2-O-desulfated glycosaminoglycan derivative with a iduronic acid desulfation degree not greater than 60% of the total uronic units, which has the following formula:

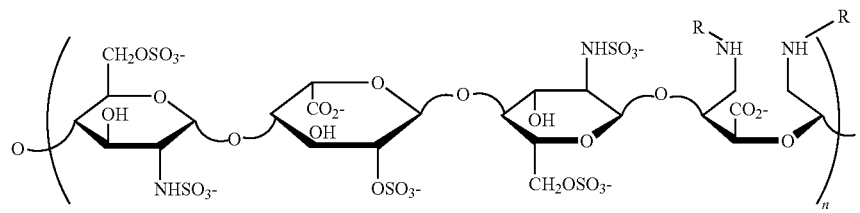

where R are different and are H or $CH_2COO^-$ and where n is 10.

8. A method of treating a pathological state due to abnormal angiogenesis, comprising administering to a subject suffering from abnormal angiogenesis a 2-O-desulfated glycosaminoglycan derivative with a iduronic acid desulfation degree not greater than 60% of the total uronic units, which has the following formula:

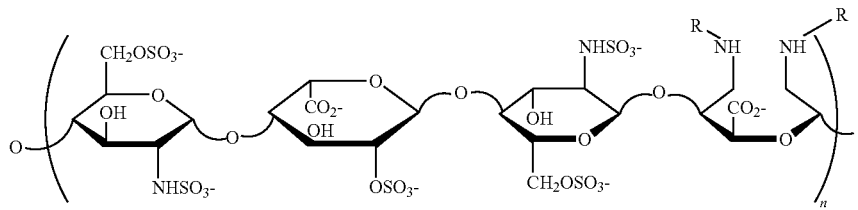

where R are different and are H or $CH_2CH_2SO_3^-$ and n is 10.

9. The method of claim 5, wherein the abnormal angiogenesis is a tumor, a tumor associated with metastases, tumor metastases, diabetic retinopathy, retrolenticular fibroplasias, psoriasis or restenosis after angioplasty or after coronary bypass.

10. The method of claim 7, wherein the abnormal angiogenesis is a tumor, a tumor associated with metastases, tumor metastases, diabetic retinopathy, retrolenticular fibroplasias, psoriasis or restenosis after angioplasty or after coronary bypass.

11. The method of claim 8, wherein the abnormal angiogenesis is a tumor, a tumor associated with metastases, tumor metastases, diabetic retinopathy, retrolenticular fibroplasias, psoriasis or restenosis after angioplasty or after coronary bypass.

* * * * *